(12) United States Patent
Littlejohn (10) Patent No.: US 12,220,298 B2
(45) Date of Patent: Feb. 11, 2025

(54) APPARATUS AND METHOD FOR PROSTHODONTICS

(71) Applicant: Alexander Littlejohn, Glasgow (GB)

(72) Inventor: Alexander Littlejohn, Glasgow (GB)

( * ) Notice: Subject to any disclaimer, the term of this patent is extended or adjusted under 35 U.S.C. 154(b) by 1040 days.

(21) Appl. No.: 16/970,192

(22) PCT Filed: Feb. 14, 2019

(86) PCT No.: PCT/GB2019/050394
§ 371 (c)(1),
(2) Date: Aug. 14, 2020

(87) PCT Pub. No.: WO2019/158925
PCT Pub. Date: Aug. 22, 2019

(65) Prior Publication Data
US 2021/0077231 A1  Mar. 18, 2021

(30) Foreign Application Priority Data

Feb. 14, 2018 (GB) ..................................... 1802402

(51) Int. Cl.
*A61C 9/00* (2006.01)
*A61C 13/00* (2006.01)
(Continued)

(52) U.S. Cl.
CPC .......... *A61C 9/0086* (2013.01); *A61C 9/0006* (2013.01); *A61C 13/0004* (2013.01);
(Continued)

(58) Field of Classification Search
CPC . A61C 9/0086; A61C 9/0006; A61C 13/0004; A61B 8/00; A61B 8/12;
(Continued)

(56) References Cited

U.S. PATENT DOCUMENTS 3,358,696 A * 12/1967 Littlejohn ................. A45D 2/00
                                                         132/210
3,838,513 A * 10/1974 Katz ..................... A61C 13/0001
                                                         433/171
(Continued)

FOREIGN PATENT DOCUMENTS

| EP | 2862519 A1 | 4/2015 |
|---|---|---|
| JP | S6055937 A | 4/1985 |
| JP | 6119013 B1 | 4/2017 |

OTHER PUBLICATIONS

Pisseloup, Arnaud, European Patent Office International Search Report in PCT/GB2019/050394 dated Apr. 24, 2019.

*Primary Examiner* — Matthew M Nelson
(74) *Attorney, Agent, or Firm* — Cherskov Playnik & Gurda, LLC (57) ABSTRACT

The invention relates to a dental tray assembly for intraoral imaging of an edentulous dental arch and/or palate. The dental tray assembly includes a base surface and an opposing external surface. An anterior wall is connected to the base surface and extends arcuately either side of a central axis coinciding, in use, with the labial frenulum. A posterior edge connects opposing sides of the anterior wall. The base surface and the anterior wall together define a concave trough for at least partially surrounding an edentulous arch. A spaced-apart array of ultrasound imaging elements is attached to the dental tray within the trough for emitting and receiving ultrasound signals, the received ultrasound signals being representative of the surface topography and/or subsurface structures of an edentulous dental arch and/or palate to be imaged. Advantageously, by distributing the array of ultrasound imaging elements across the surface area of dental tray the entire edentulous arch and/or palate can be imaged instantaneously. Optionally, received ultrasound signals can be communicated to a remote device, such as a (Continued)

smartphone, running a software App which processes signals to form a virtual digital impression of the dental arches enabling the manufacture of prosthetic dentures having enhanced comfort and stability.

18 Claims, 4 Drawing Sheets

(51) Int. Cl.
 *A61B 8/00* (2006.01)
 *A61B 8/12* (2006.01)
 *B06B 1/02* (2006.01)

(52) U.S. Cl.
 CPC .............. *A61B 8/12* (2013.01); *A61B 8/4254* (2013.01); *A61B 8/4455* (2013.01); *A61B 8/4472* (2013.01); *A61B 8/56* (2013.01); *B06B 1/02* (2013.01)

(58) Field of Classification Search
 CPC ... A61B 8/4254; A61B 8/4455; A61B 8/4472; A61B 8/56; B06B 1/02
 See application file for complete search history.

(56) References Cited

U.S. PATENT DOCUMENTS

| | | | | |
|---|---|---|---|---|
| 4,043,181 | A * | 8/1977 | Nigam | G01S 7/52033 73/614 |
| 4,144,882 | A * | 3/1979 | Takemoto | A61C 17/20 433/32 |
| 4,610,255 | A * | 9/1986 | Shimura | G01H 3/125 600/443 |
| 5,006,984 | A * | 4/1991 | Steele | A61B 10/00 600/587 |
| 5,269,309 | A * | 12/1993 | Fort | G01S 15/8993 600/447 |
| 5,549,924 | A * | 8/1996 | Shlenker | A61F 6/04 427/407.1 |
| 5,630,419 | A * | 5/1997 | Ranalletta | A61B 8/00 600/459 |
| 5,679,399 | A * | 10/1997 | Shlenker | A61F 6/04 427/407.1 |
| 5,680,863 | A * | 10/1997 | Hossack | G10K 11/32 600/459 |
| 5,735,282 | A * | 4/1998 | Hossack | A61B 8/4281 600/458 |
| 5,755,571 | A * | 5/1998 | Companion | A61C 19/043 33/514 |
| 6,033,222 | A * | 3/2000 | Schneider | A61C 13/082 264/20 |
| 6,039,694 | A * | 3/2000 | Larson | A61B 8/4281 73/644 |
| 6,050,821 | A * | 4/2000 | Klaassen | A61C 9/0086 433/214 |
| 6,132,378 | A * | 10/2000 | Marino | A61B 8/4281 600/459 |
| 6,638,219 | B1 * | 10/2003 | Asch | A61C 9/0086 600/587 |
| 7,175,599 | B2 * | 2/2007 | Hynynen | A61B 8/0808 600/443 |
| 7,223,249 | B2 * | 5/2007 | Rosenberg | A61B 5/103 600/587 |
| 7,285,093 | B2 * | 10/2007 | Anisimov | A61B 8/0875 600/443 |
| 7,440,788 | B2 * | 10/2008 | Jenkins | A61B 5/682 600/340 |
| 7,748,273 | B2 * | 7/2010 | Halevy-Politch | A61B 8/0875 73/598 |
| 7,766,658 | B2 * | 8/2010 | Tricca | A61B 5/0088 433/80 |
| 7,947,508 | B2 * | 5/2011 | Tricca | A61B 5/0088 436/163 |
| 8,075,309 | B2 * | 12/2011 | Li | A61P 1/02 433/80 |
| 8,612,037 | B2 * | 12/2013 | Powell | G05B 15/02 433/172 |
| 8,753,121 | B2 * | 6/2014 | Gharib | A61C 17/0202 433/81 |
| 9,492,244 | B2 * | 11/2016 | Bergheim | A61C 5/62 |
| 9,504,536 | B2 * | 11/2016 | Bergheim | A61C 1/0061 |
| 9,675,426 | B2 * | 6/2017 | Bergheim | A61C 5/40 |
| 9,877,700 | B1 * | 1/2018 | Asch | A61B 8/4427 |
| 9,877,801 | B2 * | 1/2018 | Khakpour | A61C 1/087 |
| 10,098,717 | B2 * | 10/2018 | Bergheim | A61C 1/07 |
| 10,363,120 | B2 * | 7/2019 | Khakpour | A61C 17/024 |
| 10,603,008 | B2 * | 3/2020 | Maev | A61C 19/04 |
| 10,722,325 | B2 * | 7/2020 | Khakpour | A61C 17/028 |
| 10,799,210 | B1 * | 10/2020 | Zhang | A61C 9/0086 |
| 10,806,544 | B2 * | 10/2020 | Khakpour | A61C 5/40 |
| 10,835,355 | B2 * | 11/2020 | Gharib | A61C 17/0202 |
| 11,045,166 | B2 * | 6/2021 | Gerbaulet | A61B 5/4542 |
| 11,116,568 | B2 * | 9/2021 | Katzberg | A61B 8/12 |
| 11,173,019 | B2 * | 11/2021 | Bergheim | A61C 17/028 |
| 11,350,993 | B2 * | 6/2022 | DiVito | A61N 5/0624 |
| 11,382,727 | B1 * | 7/2022 | Marghalani | A61B 1/247 |
| 2001/0021807 | A1 * | 9/2001 | Saito | G10K 11/02 600/459 |
| 2002/0068871 | A1 * | 6/2002 | Mendlein | A61B 8/4209 600/459 |
| 2002/0153805 | A1 * | 10/2002 | Smith | G01N 29/348 310/311 |
| 2003/0138754 | A1 * | 7/2003 | DiMarino | A61C 9/0006 433/37 |
| 2003/0149359 | A1 * | 8/2003 | Smith | A61B 8/4281 600/437 |
| 2004/0100163 | A1 * | 5/2004 | Baumgartner | B06B 1/0622 310/334 |
| 2004/0219486 | A1 * | 11/2004 | Heasley | A61C 3/10 433/136 |
| 2005/0074723 | A1 * | 4/2005 | Ostler | A61C 5/64 433/215 |
| 2005/0244792 | A1 * | 11/2005 | Verdi | A61C 19/066 433/215 |
| 2007/0065782 | A1 * | 3/2007 | Maschke | A61C 3/00 433/224 |
| 2007/0078345 | A1 * | 4/2007 | Mo | A61B 8/12 600/459 |
| 2007/0172112 | A1 * | 7/2007 | Paley | A61C 13/0022 382/128 |
| 2007/0190481 | A1 * | 8/2007 | Schmitt | A61C 9/0046 433/68 |
| 2008/0021327 | A1 * | 1/2008 | El-Bialy | A61C 8/0006 600/459 |
| 2008/0254405 | A1 * | 10/2008 | Montgomery | A61C 19/06 433/29 |
| 2008/0311540 | A1 * | 12/2008 | Gottenbos | A61C 17/20 433/86 |
| 2008/0311545 | A1 * | 12/2008 | Ostler | A61C 19/066 433/216 |
| 2009/0011385 | A1 * | 1/2009 | Jensen | A61C 1/07 433/119 |
| 2009/0306506 | A1 * | 12/2009 | Heger | A61C 9/0086 600/443 |
| 2010/0035201 | A1 * | 2/2010 | Beck | A61C 1/084 433/76 |
| 2010/0112526 | A1 * | 5/2010 | Keller | A61B 18/20 424/53 |
| 2010/0210943 | A1 * | 8/2010 | Mahmoud | A61B 8/4245 600/437 |
| 2010/0277040 | A1 * | 11/2010 | Klee | H10N 30/2047 29/25.35 |
| 2011/0060558 | A1 * | 3/2011 | Pettersson | A61C 13/0004 703/1 |
| 2011/0196653 | A1 * | 8/2011 | Lajoie | A61C 13/0004 703/1 |
| 2012/0064477 | A1 * | 3/2012 | Schmitt | A61C 9/0053 433/44 |

(56) References Cited

U.S. PATENT DOCUMENTS

| | | | |
|---|---|---|---|
| 2012/0179281 A1* | 7/2012 | Steingart | A61C 13/10 703/11 |
| 2012/0244489 A1* | 9/2012 | Carnahan | A61B 8/0875 433/25 |
| 2013/0040264 A1* | 2/2013 | Scurtescu | A61C 7/00 433/119 |
| 2013/0289950 A1* | 10/2013 | Kopelman | A61C 8/0001 703/1 |
| 2014/0321244 A1* | 10/2014 | Lee | A61B 8/4444 367/180 |
| 2014/0329194 A1* | 11/2014 | Sachdeva | A61C 7/002 433/24 |
| 2015/0132718 A1* | 5/2015 | Kerschensteiner | A61C 13/01 433/199.1 |
| 2015/0238345 A1* | 8/2015 | Decker | A61C 5/007 382/128 |
| 2015/0313572 A1* | 11/2015 | Gerbaulet | A61C 19/04 433/29 |
| 2016/0207068 A1* | 7/2016 | Dekker | G10K 11/004 |
| 2016/0317264 A1* | 11/2016 | Derraugh | A61C 9/0053 |
| 2017/0043375 A1* | 2/2017 | Weekamp | H10N 30/302 |
| 2017/0065372 A1* | 3/2017 | Mah | A61N 5/0601 |
| 2017/0100219 A1* | 4/2017 | Schmitt | A61B 5/0022 |
| 2017/0215997 A1* | 8/2017 | Martin | A61B 5/6835 |
| 2017/0258560 A1* | 9/2017 | Llop | A61C 9/0006 |
| 2018/0130457 A1* | 5/2018 | Hakkens | A61N 7/022 |
| 2018/0206957 A1* | 7/2018 | Ruth | A61C 7/023 |
| 2018/0221248 A1* | 8/2018 | Maurer | A61C 9/0006 |
| 2018/0250099 A1* | 9/2018 | Lai | A61C 7/08 |
| 2018/0338819 A1* | 11/2018 | Chou | A61C 7/08 |
| 2018/0368952 A1* | 12/2018 | Chou | A61C 19/05 |
| 2018/0373913 A1* | 12/2018 | Panchawagh | H10K 59/65 |
| 2019/0000599 A1* | 1/2019 | Hanuschik | A61H 17/0211 |
| 2019/0102880 A1* | 4/2019 | Parpara | B29C 51/46 |
| 2019/0105842 A1* | 4/2019 | Dau | B33Y 50/00 |
| 2019/0125297 A1* | 5/2019 | Chan | A61B 6/481 |
| 2019/0254789 A1* | 8/2019 | Lancelle | A61C 9/0046 |
| 2019/0298280 A1* | 10/2019 | Takada | A61B 6/52 |
| 2019/0328353 A1* | 10/2019 | Hendriks | A61B 8/0891 |
| 2020/0008299 A1* | 1/2020 | Tran | H05K 1/0386 |
| 2020/0046476 A1* | 2/2020 | Li | A61C 19/06 |
| 2020/0368973 A1* | 11/2020 | Van Esbroeck | B29C 64/124 |
| 2020/0406299 A1* | 12/2020 | Hughes | B06B 1/0622 |
| 2021/0045851 A1* | 2/2021 | Duret | A61C 9/0006 |
| 2021/0077231 A1* | 3/2021 | Littlejohn | A61C 9/0086 |
| 2021/0085436 A1* | 3/2021 | Evans | A61C 17/228 |
| 2021/0127979 A1* | 5/2021 | Binkowski | A61C 7/002 |
| 2021/0186820 A1* | 6/2021 | Chakraborty | A61C 7/002 |
| 2021/0196436 A1* | 7/2021 | Raby | B29C 64/00 |
| 2021/0366136 A1* | 11/2021 | Lancelle | A61C 13/34 |
| 2021/0386527 A1* | 12/2021 | Choi | A61C 9/0053 |
| 2021/0401551 A1* | 12/2021 | Kim | B33Y 80/00 |
| 2022/0071739 A1* | 3/2022 | Hwang | A61C 7/008 |
| 2022/0087791 A1* | 3/2022 | Choi | A61C 19/05 |
| 2022/0168078 A1* | 6/2022 | Klingenburg | A61C 9/0006 |
| 2022/0175499 A1* | 6/2022 | DiMarino | A61C 9/002 |
| 2022/0226201 A1* | 7/2022 | Hoffmann | A61K 6/90 |
| 2022/0313402 A1* | 10/2022 | Katzman | A61C 7/002 |
| 2022/0401191 A1* | 12/2022 | Chawich | A61C 9/0013 |
| 2022/0401192 A1* | 12/2022 | Marks | A61C 9/0053 |
| 2023/0026846 A1* | 1/2023 | Hansen | A61C 13/0004 |
| 2023/0043519 A1* | 2/2023 | Choi | G16H 50/50 |
| 2023/0055910 A1* | 2/2023 | Rosenberg | A61B 5/4552 |
| 2023/0070296 A1* | 3/2023 | Karaceper | A61C 9/0026 |
| 2023/0097249 A1* | 3/2023 | Dekel | A61C 9/0006 433/29 |
| 2023/0126119 A1* | 4/2023 | Koski | A61C 9/0006 433/214 |
| 2023/0130834 A1* | 4/2023 | Willoughby | B33Y 80/00 433/6 |
| 2023/0153476 A1* | 5/2023 | Fabbri | G06F 30/17 706/47 |
| 2023/0190424 A1* | 6/2023 | Bonding | A61C 9/0006 345/419 |
| 2023/0263591 A1* | 8/2023 | Fares | A61C 1/082 433/226 |
| 2023/0263604 A1* | 8/2023 | Wilstead | A61C 9/0006 433/71 |
| 2023/0263605 A1* | 8/2023 | Madden | A61C 13/34 264/16 |
| 2023/0320823 A1* | 10/2023 | Marshall | A61C 19/045 433/69 |
| 2023/0346532 A1* | 11/2023 | Fernández Fajardo | A61F 5/566 |
| 2023/0351712 A1* | 11/2023 | Stoot | A61C 7/002 |
| 2023/0390026 A1* | 12/2023 | Rieger | B33Y 30/00 |
| 2023/0390027 A1* | 12/2023 | Marshall | G16H 20/30 |
| 2023/0390040 A1* | 12/2023 | Sun | A61K 6/62 |
| 2024/0028782 A1* | 1/2024 | Selberis | G16H 50/20 |
| 2024/0033061 A1* | 2/2024 | Hultgren | A61C 19/045 |

* cited by examiner

APPARATUS AND METHOD FOR PROSTHODONTICS

PRIORITY CLAIM

The instant application is a nationalization of PCT/GB2019/050394, filed on Feb. 14, 2019, presently pending, which in turn claimed priority to British application 1802402.6, filed on Feb. 14, 2018, presently pending, the contents of each application is hereby incorporated by reference.

TECHNICAL FIELD

The present invention relates to the field of prosthodontics and particularly, though not exclusively, to a dental tray assembly for collecting data for imaging a patient's edentulous arches and palate; and to a method of imaging edentulous arches and palate for use in the subsequent design and manufacture of dental prostheses.

DESCRIPTION

Conventional methods for the design and manufacture of dental prostheses typically require the creation of physical impressions of a patient's arches. This is a manual process which involves preparing a suitable impression compound, e.g. in the form of a paste, and placing it within an impression tray which is then applied to the edentulous arches and allowed to set.

There are numerous disadvantages associated with conventional methods. For example, it is typically necessary for a patient to attend multiple dental appointments over a period of several weeks. Various positive and negative moulds are produced during successive appointments to create custom-fit trays, to determine bite position, to produce finalised prostheses, and then to test their fit and make any necessary minor adjustments. The use of viscous impression materials means the procedure is often messy, may be uncomfortable, is inevitably time-consuming for both the patient and practitioner, and is expensive.

Ultimately, the comfort and stability of prosthetic dentures rely on a highly accurate match between the interface of the prosthesis and the corresponding surface topography of a patient's arches. Conventional techniques may not always provide a match of sufficient accuracy due to the multiple opportunities for human error within the overall process. Unintended movement of the impression tray within the oral cavity, premature removal of the impression tray, and the presence of air bubbles within the impression material are just three possible ways in which errors can arise.

Moreover, such conventional techniques are incapable of detecting subsurface features of the edentulous arches such as variations in gum tissue depth relative to the underlying bone at any given point. Ignoring subsurface features of the edentulous arches may result in an uneven transmission of mechanical stresses at the interface between the prosthesis and the underlying soft tissue of the edentulous arches. This may result in patient discomfort and possible rejection of prostheses.

More recently, intraoral digital scanning techniques have been developed whereby a hand-held wand is inserted into the oral cavity to produce near instantaneous virtual impressions without the need for physical contact with intraoral palate. One such scanner is the TRIOS® scanner offered by Danish firm, 3Shape A/S. Ultrasonic imaging probes are also known which employ piezoelectric transducers to produce virtual impressions. Such digital scanners help to eliminate some of the aforementioned instances of human error which arise when prostheses are manufactures on the basis of physical impressions. By providing manufacturing labs with more precise and reliable representations of the oral topography which are not reliant on multi-step manual processes, accuracy can be improved.

However, hand-held digital scanners typically require a practitioner to manually manoeuvre a bulky scanning head around the mouth to cumulatively build a rendered image of the overall intraoral cavity and edentulous arches. This typically involves manually distorting the lips and cheeks and associated muscles to enable the scanning head to image the gingival sulci. Moreover, whilst intraoral scanners are capable of capturing highly accurate images of the dentulous mouth, they are less capable of doing so for the edentulous mouth due to the relative absence of fixed reference points.

In recognising the drawbacks of existing intraoral scanning techniques, the inventor of the present invention has devised a new apparatus and associated method which overcomes, or at least ameliorates, one or more of the aforementioned problems.

According to a first aspect of the present invention there is provided a dental tray assembly for intraoral imaging of an edentulous dental arch and/or palate; the dental tray assembly comprising:
  (i) a base surface for facing, in use, a dental arch within an oral cavity;
  (ii) an opposing external surface;
  (iii) an anterior wall connected to said base surface and extending arcuately either side of a central axis coinciding, in use, with the labial frenulum; and
  (iv) a posterior edge connecting opposing sides of the anterior trough wall and extending, in use, substantially perpendicular to the central axis;
wherein the base surface and the anterior wall together define a concave trough for at least partially surrounding, in use, a dental arch within an oral cavity; and wherein a spaced-apart array of ultrasound imaging elements is attached to the dental tray within the trough for emitting and receiving ultrasound signals, the received ultrasound signals being representative of the surface topography and/or subsurface structures of an edentulous dental arch and/or palate to be imaged.

It will be appreciated that each imaging element is located within the base and/or anterior wall of the trough to thereby define a series of fixed imaging reference points.

Optionally, the array of ultrasound imaging elements are spaced apart across the entirety of the base surface and/or the anterior wall.

It will be appreciated that by distributing the imaging elements across a wide surface area of the dental tray, this allows for simultaneously imaging of multiple locations within an edentulous arch and/or palate, i.e. the entire arch and/or palate can be imaged substantially instantaneously.

Optionally, a gel-filled sac is removably locatable within the arcuate trough to provide a deformable interface between the dental tray and a patient's edentulous arches and/or palate.

Optionally, the gel is a water-based gel.

Alternatively, the gel within the gel-filled sac is a heat-sensitive settable gel for forming an impression of anatomical surface features of the oral cavity including one or more of the group comprising the palate, ridges and sulci.

Optionally, the sac is formed from a synthetic latex material.

It will be appreciated that employing a water-based gel as an interface between the ultrasound imaging elements and the edentulous arches and palate will help to eliminate undesirable reflection of ultrasound waves. Any distortion in the ultrasound signals can be minimised by ensuring that the acoustic impedance value of the gel material is substantially matched to that of the edentulous arches and palate.

Optionally, the gel-filled sac is dimensioned such that it fills the arcuate trough and extends above the height of the anterior trough wall.

It will be appreciated that the deformable nature of the gel will gently conform to the natural surface topography of the edentulous arches and palate whilst also ensuring that no part of the dental tray will directly contact a patient's edentulous arches and/or palate during use.

Optionally, the gel-filled sac comprises an attached sheath adapted to envelop the dental tray.

Optionally, the ultrasound imaging elements are non-piezoelectric.

Optionally, the ultrasound imaging elements are printed on a flexible foil which is conformable to the concave internal surface of the dental tray.

It will be appreciated that the flexible foil may additionally be overlaid on one or more of the external concave surfaces of the dental tray.

Optionally, a handle portion projects away from the anterior trough wall and, in use, extends out of the oral cavity.

Optionally, a camera is located on the handle for detecting, in use, the position of reference points on a patient's face relative to a patient's mouth.

It will be appreciated that the camera viewing angle will be determined by its position on the handle and/or the length of the handle so as to be directed towards, for example, the eyes and/or nose and/or ears of a patient. Other suitable fixed facial landmarks such as, but not limited to, freckles, moles, scars etc may also be used.

Optionally, the ultrasound imaging elements are connected to a power source located in the handle portion.

It will be appreciated that the ultrasound imaging elements may alternatively be connectable to an external power source, via a power cord.

Optionally, an aperture is formed in the anterior trough wall to facilitate a physical connection between the power source and the ultrasound imaging elements.

Optionally, the ultrasound imaging elements are connectable to an external processing device.

Optionally, the camera is connectable to an external processing device.

Optionally, the external processing device is a mobile or tablet device.

According to a second aspect of the present invention there is provided a method of imaging edentulous arches and/or palate comprising the steps of:
(i) providing a dental tray in accordance with the first aspect;
(ii) locating a gel-filled sac within the arcuate trough of the dental tray to provide a deformable interface between it and a dental arch and/or palate to be imaged;
(iii) applying a layer of gel to the exposed surface of the gel-filled sac;
(iv) introducing the dental tray into the oral cavity and moving it towards the dental arch and/or palate to be imaged such that the gel-filled sac is gently urged against and conforms to the shape of said dental arch and/or palate;
(v) activating the spaced-apart array of ultrasound imaging elements within the trough of the dental tray; and
(vi) receiving a primary data set from the ultrasound imaging elements representative of the sub-surface structures of the dental arch and/or palate to be imaged.

Optionally, the step of receiving a primary data set from the ultrasound imaging elements includes processing said data in a processing device.

Optionally, the step of processing the primary data set includes storing the processed data set in a memory for future use.

Optionally, the step of processing the primary data set includes providing a display for displaying a synchronous rendered image of a patient's edentulous arches and/or palate.

It will be appreciated that the primary data set may be processed remotely on, for example, a smartphone, tablet device or other ancillary device. A three-dimensional image may be displayed showing sub-surface features of the edentulous arches and/or palate. The images may be manipulated by software to show a realistic coloured rendered image of the soft tissue in its existing relaxed form. From this, it is possible to determine tissue depth relative to the underlying bone at any given point thus enabling the design of bespoke prostheses which compress the soft tissue to an optimal degree for comfort, stability and retention within a patient's mouth.

The dental trays and gel-filled sacs according to the present invention may be purchased by a patient such that the method of imaging the edentulous arches and/or palate can be performed outside of a clinical environment, e.g. at home. Advantageously, the apparatus of the present invention may be used by a patient to image their own edentulous arches and/or palate and place a remote order for replacement prosthesis using a software App on a smartphone, tablet or other device.

Optionally, the step of locating a gel-filled sac within the arcuate trough of the dental tray is preceded by a step of enveloping the dental tray in a protective sheath.

Alternatively, the step of locating a gel-filled sac within the arcuate trough of the dental tray includes enveloping the dental tray in a protective sheath which is formed integrally with the gel-filled sac.

It will be appreciated that enveloping the dental tray with a protective sheath provides a hygienic barrier facilitating re-use of the dental tray by different patient.

Optionally, the step of locating a gel-filled sac within the arcuate trough includes providing a heat-settable gel-filled sac; subjecting the gel-filled sac to natural intraoral heating; and allowing it to set thus forming a durable impression of the imaged dental arch and/or palate.

Optionally, the method includes the subsequent steps of removing the dental tray from an oral cavity; digitally scanning the set impression to obtain a secondary data set representative of the surface topography of a dental arch and/or palate; and combining said primary and secondary data sets to provide a composite rendered image of both surface and sub-surface features of the edentulous arches and/or palate.

It will be appreciated that dental prostheses manufactured using virtual/digital impressions can be created very accurately when those impressions are formed from a composite or hybrid data set. In particular, the interface fit between such prostheses and a patient's intra-oral surfaces can be greatly improved. By both accurately matching the surface topography of the edentulous arches and adjoining palate; and by taking due account of substructure features such as the depth variation of soft tissues relative to underlying bone structures, mechanical stresses during use are balanced and patient discomfort and instances of patient rejection of prostheses are eliminated, or at least minimised. Furthermore, a rendered image of the entirety of the edentulous arches and/or palate can be obtained substantially instantaneously. This constitutes improvement upon existing digital scanners which typically require a scanning head of a hand-held wand to be manually manoeuvred around the edentulous arches in a progressive fashion to form a cumulative rendered image only once a sufficient number of reference points have been identified within the oral cavity.

Optionally, the method includes the further step of activating the camera to capture facial feature data which is then processed with said primary and secondary data sets.

It will be appreciated that capturing facial data, including the relative positions of a patient's eyes and nose (or other suitable anatomical landmarks), can help determine the proper position of the teeth on a prosthesis to be manufactured. Since the camera is located at a fixed position relative to the ultrasound imaging elements, by also determining the relative positions of a patient's eyes and/or nose (or other suitable anatomical landmark), this enables the position of the teeth to be approximated by software means.

According to a third aspect of the present invention there is provided a method of producing a dental prosthesis comprising providing a computer-readable medium having computer-executable instructions adapted to cause a 3D printer or milling machine to print a dental prosthesis, wherein the computer-executable instructions are created using a data set obtained by the second aspect.

Further features and advantages of the first, second and third aspects of the present invention will become apparent from the claims and the following description.

BRIEF DESCRIPTION OF DRAWINGS

Embodiments of the present invention will now be described by way of example only, with reference to the following diagrams, in which.

DETAILED DESCRIPTION

Figure 1:
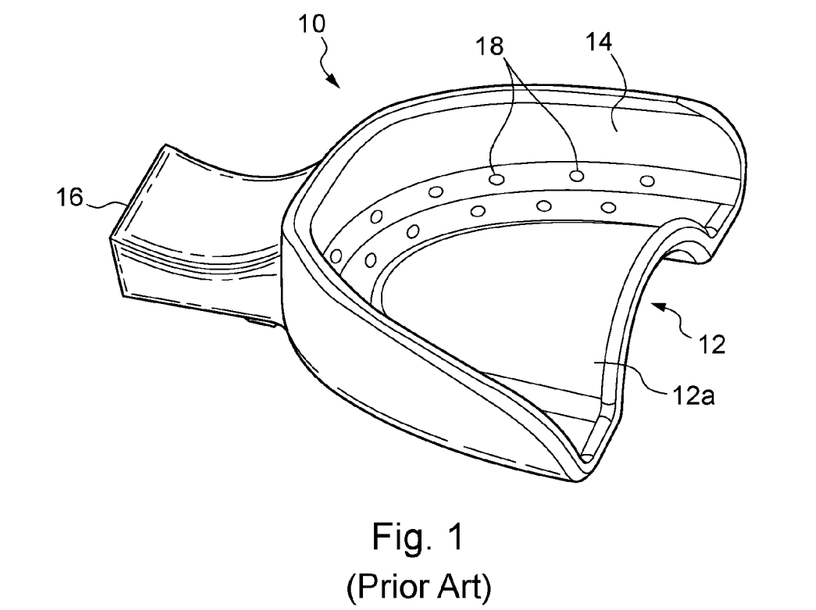
FIG. 1 shows a known dental impression tray used in conventional methods for the design and manufacture of dental prostheses.

FIG. 1 shows a conventional dental impression tray 10 comprising a base 12, an arcuate anterior wall 14 upstanding from the base, and a graspable handle 16 extending perpendicularly away from a midpoint of the arcuate anterior wall 14. The base 12 is provided with a central bulbous protrusion 12a and a plurality of apertures 18. A posterior edge 20 connects the opposing ends 14e of the arcuate anterior wall 14. Together, the base 12, 12a and the arcuate anterior wall 14 define a tray-like receptacle for receiving a quantity of viscous impression material (not shown) to facilitate the taking of an impression of the entire upper dental arch and/or palate of a patient. Some of the viscous impression material extends into the apertures 18 and so a mechanical coupling is provided once the material sets to retain the impression material on the tray 10.

Figures 2A, 2B:
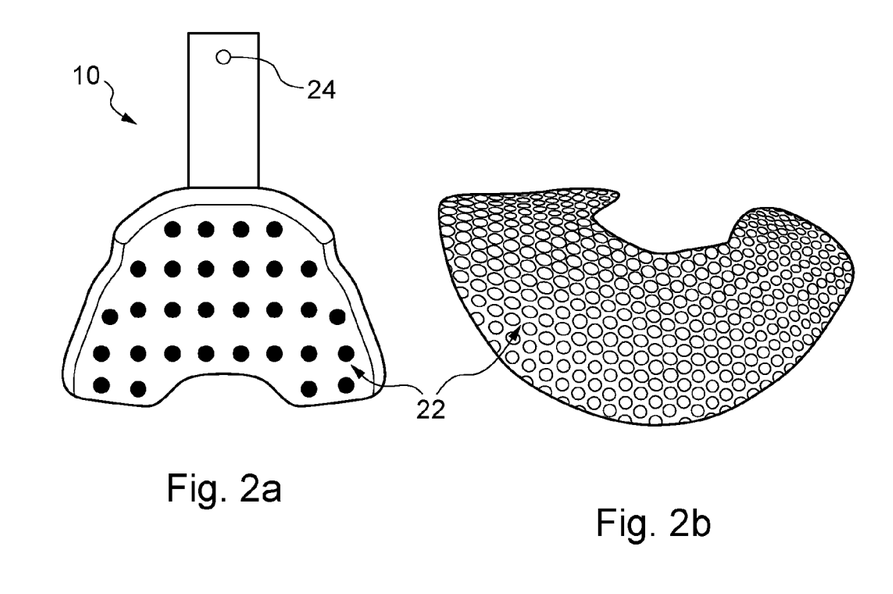
FIG. 2a is a schematic plan view of a dental impression tray according to an embodiment of the present invention incorporating a spaced-apart array of ultrasound imaging elements.
FIG. 2b shows the ultrasound imaging elements 22 printed on a thin flexible foil.

FIG. 2a is a schematic plan view of a dental impression tray 10 according to an embodiment of the present invention. The dental tray 10 is similar in construction to that of the conventional tray of FIG. 1. However, it is differentiated insofar as it is provided with a spaced-apart array of low-power ultrasound imaging elements 22 on its base 12. In alternative embodiments (not shown), ultrasound imaging elements 22 are additionally provided on the outer and/or inner side surfaces of the arcuate anterior wall 14. The transducers of the ultrasound imaging elements 22 are printed on a thin flexible foil (see FIG. 2b) which can readily conform to the surface profile of the base 10 and the side surfaces of the arcuate anterior wall 14 and be fixedly attached thereto.

Each of the ultrasound imaging elements 22 is connected to a power source (not shown) and a printed circuit board (not shown) located in a cavity formed inside the graspable handle 16 which also houses the electronic circuitry for operating the ultrasound imaging elements 22 and the camera 25. A control button 24 is provided towards the anterior end of the upper surface of the handle 16 for activating the ultrasound imaging elements 22. It will be appreciated that in some embodiments (not shown), the ultrasound imaging elements 22 may be activated automatically (or remotely) once the dental tray 10 is correctly positioned in the mouth, thereby obviating the need for a control button.

Figure 3:
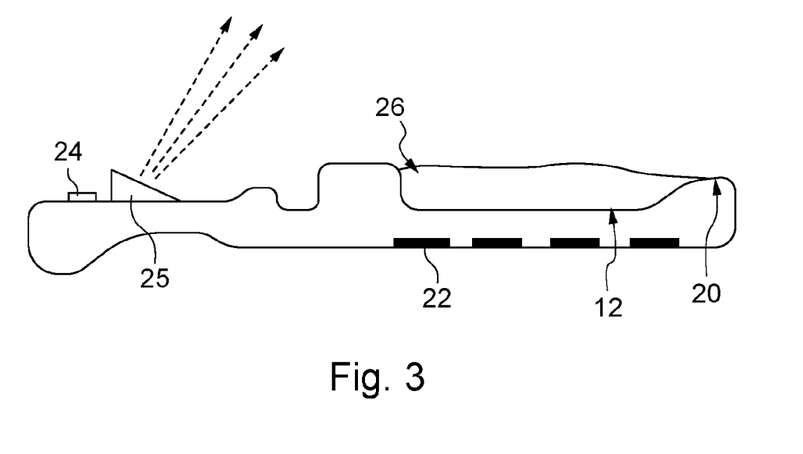
FIG. 3 is a partial cross-sectional side view of the dental impression tray of FIG. 2 holding a gel-filled sac.

FIG. 3 is a partial cross-sectional side view of a modified version of the dental impression tray 10 of FIG. 2. The modified version is provided with a miniature camera 25 provided towards the anterior end of the upper surface of the handle 16 proximate the control button 24. The camera 25 is orientated at an angle of inclination such that its field of view is wide enough to encompass various anatomical landmarks of a patient's face including, for example, the eyes and nose.

Also shown in FIG. 3 is a gel-filled sac 26 located within the tray-like receptacle defined by the base 12 and the arcuate anterior wall 14. In some embodiments, the gel is any water-based gel acceptable for intraoral use; and the sac is formed from a thin synthetic latex sheath. The gel-filled sac 26 is therefore deformable and dimensioned such that, in its relaxed state, it substantially fills the tray-like receptacle and extends slightly above the height of at least a portion of the arcuate anterior wall 14. In an alternative embodiment, the gel-filled sac 26 comprises a heat-sensitive settable gel which sets when exposed to intraoral heat for a sufficient time period.

In some embodiments, a secondary sheath (not shown) envelopes the dental impression tray 10. The secondary sheath may be formed integrally with the gel-filled sac 26;

or provided as a separate part. In either case, all surfaces of the dental impression tray 10 are covered thus allowing its re-use by different patients.

Figure 4:
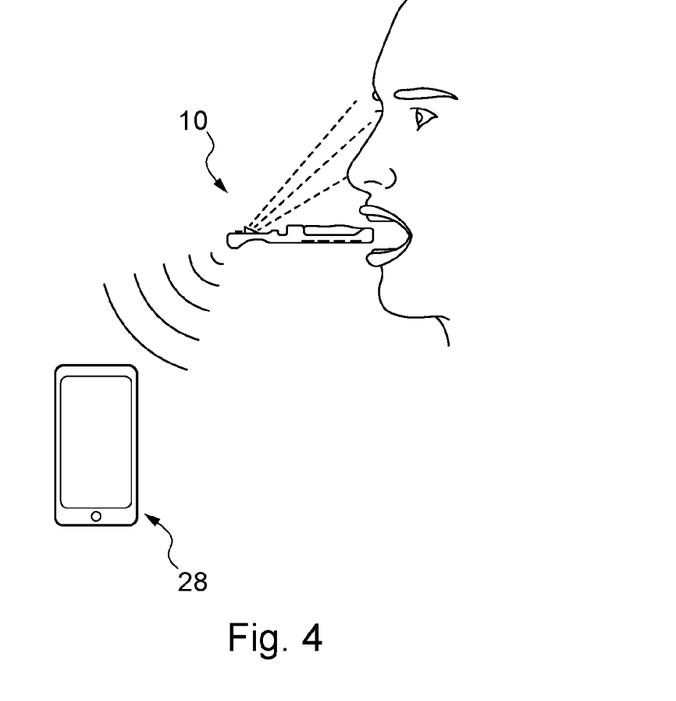
FIG. 4 is a schematic representation showing the dental impression tray of FIG. 3 in use.
Figure 5:
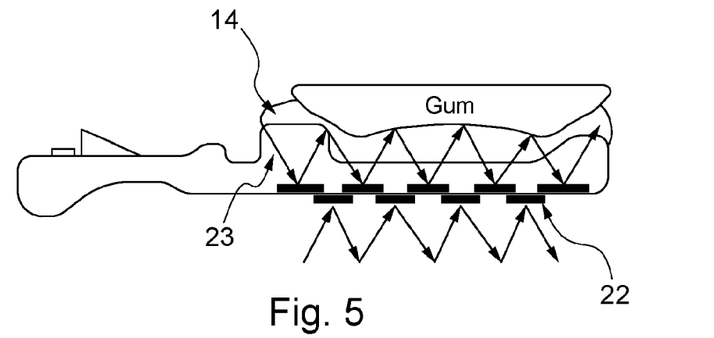
FIG. 5 is a schematic view of the dental impression tray of FIG. 3 in which the gel-filled sac is urged against a patient's edentulous dental arch and palate.
Figure 6:
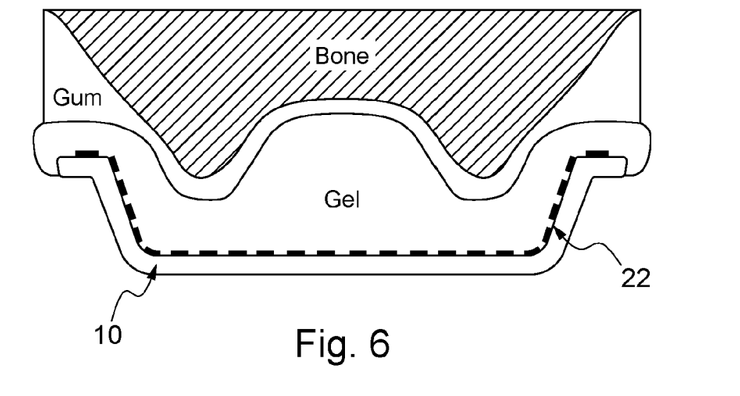
FIG. 6 is a schematic cross-sectional end view of the dental impression tray of FIG. 5 showing the underlying tissue and bone structure of a patient's edentulous dental arch.

In use, a thin sheath is arranged to envelop all exposed surfaces of the dental tray 10. A new gel-filled sac 26 is located on the base 12 of the dental tray 10 and overlies the spaced apart array of ultrasound imaging elements 22 situated on the inner side of the arcuate anterior wall 14 and/or the base 12. A further layer of water-based gel is applied to the upper surface of the gel-filled sac 26 before the dental tray 10 is inserted into a patient's oral cavity as indicated schematically in FIG. 4. The dental tray 10 is moved towards the upper maxilla such that its gel-filled sac 26 is urged against the upper dental arch and/or palate. The viscous nature of the gel-filled sac 26 allows it to deform and conform to the surface topography of the upper dental arch as shown in FIGS. 5 and 6. The gel-filled sac 26 and the additional layer of water-based gel eliminate, or at least minimise, ultrasound transmission losses.

Once correctly positioned, a dental practitioner (or the patient) may depress the control button 24 to actuate (perhaps after a delay) the spaced-apart array of ultrasound imaging elements 22. Each of the ultrasound imaging elements 22 emits a signal 23 (see FIG. 5) within the 10 MHz to 150 MHz frequency range. The received signals 23 constitute a primary data set which is communicated to a remote device, for example a smartphone 28, running a software App which processes the primary data to form a virtual digital impression of the edentulous arches and/or palate.

In a modified embodiment, a camera 25 records the positions of a patient's eyes and/or nose (or other suitable anatomical landmarks) relative to the ultrasound imaging elements 22 within the mouth. The camera 25 is also actuated by depressing the control button 24. This facial data is also communicated to the remote device 28 where it is processed along with the primary data set to allow the eventual position of prosthetic teeth to be approximated.

In a further modified embodiment, the gel-filled sac 26 comprises a heat-sensitive settable gel which sets when exposed, for a sufficient time-period, to intraoral heat. The gel adapts to the profile of the underlying tissue to thereby minimise any distorting pressure being applied on the tissue during capture of a scan.

Figure 7:
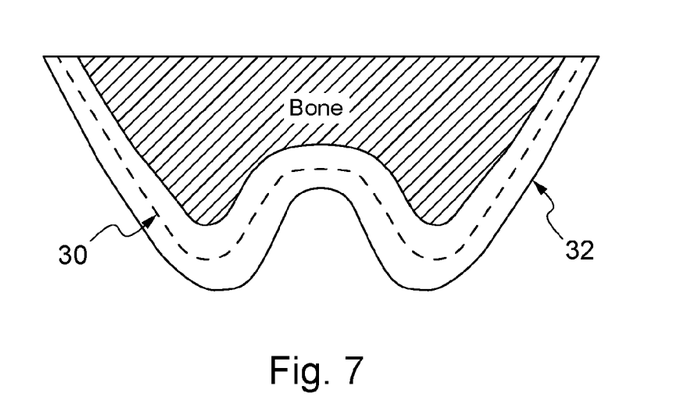
FIG. 7 is a schematic cross-sectional view through a patient's edentulous dental arch showing an optimal degree of gum compression caused by a dental prosthesis.

In some embodiments, the various data sets communicated to the remote device 28 may be processed by software to provide a rendered simulation of an optimal degree of compression 30 subjected to the soft tissue 32 of the edentulous arches and/or palate at any given point by a dental prosthesis (see FIG. 7). The rendered image can be manipulated to show further compression or relaxation of the soft tissue. The simulations can be used to assist in the design of dental prosthesis to improve their fit, stability and retention on the edentulous arches and/or palate, and hence help to promote comfort and patient acceptance.

It will be appreciated that the dental tray 10 of the present invention provides several advantages over conventional dental impression trays. Dental prostheses manufactured using virtual/digital impressions can be created very accurately, especially when those impressions are formed from a composite or hybrid data set. In particular, the interface fit between such prostheses and a patient's intra-oral surfaces can be greatly improved. By both accurately matching the surface topography of the edentulous arches and adjoining palate; and by taking due account of substructure features such as the depth variation of soft tissues relative to underlying bone structures, mechanical stresses during use are balanced and patient discomfort and instances of patient rejection of prostheses are eliminated, or at least minimised. Furthermore, a rendered image of the entirety of the edentulous arches and/or palate can be obtained substantially instantaneously. Use of the external camera 25 to collect and process facial data also provides a richer set of data which can be used to determine the size and relative positions of prosthetic teeth.

It is envisaged that the dental trays 10 and gel-filled sacs 26 may be purchased by a patient (or provided to a patient free of charge on a subscription basis) such that the method of imaging the edentulous arches and/or palate can be performed outside of a clinical environment. For example, the apparatus of the present invention may be provided as a kit for use by a patient at home to image their own edentulous arches and/or palate. A smartphone App would facilitate placing a remote order for bespoke replacement prosthesis which takes into account any changes in tissue or bone structure which may occur over time, and reduce the time, inconvenience and costs associated with the manufacture of dental prostheses.

Although a several embodiments of the invention have been disclosed herein, this has been done by way of example only. Those embodiments are not intended to be limiting with respect to the scope of the statements of invention and the appended claims. Indeed, it is contemplated by the inventor that various substitutions, alterations, and modifications may be made to the invention without departing from the scope of the invention as defined by the claims. For example, whilst the illustrated dental tray 10 is adapted for use with the edentulous arch and/or palate associated with the upper maxilla, an adapted shape can readily be adopted for use with the edentulous arch and/or palate associated with the lower mandible. Although reference throughout has been made to the edentulous arches, it will be appreciated that this term is intended to include partially edentulous arches. A plurality of ultrasound imaging elements 22 may additionally be provided on any or all of the external surfaces of the base 10 and/or arcuate anterior wall 14 of the dental tray. For example, sensors provided on the underside of the base 12 can be used to locate the antagonist, i.e. the opposing arch of the mandible or maxilla, to allow for more accurate design and positioning of a prosthetic. Bite pads provided with ultrasound imaging elements 22 to determine the location of the lower mandible relative to the upper maxilla and vice-versa.

Figure 8:
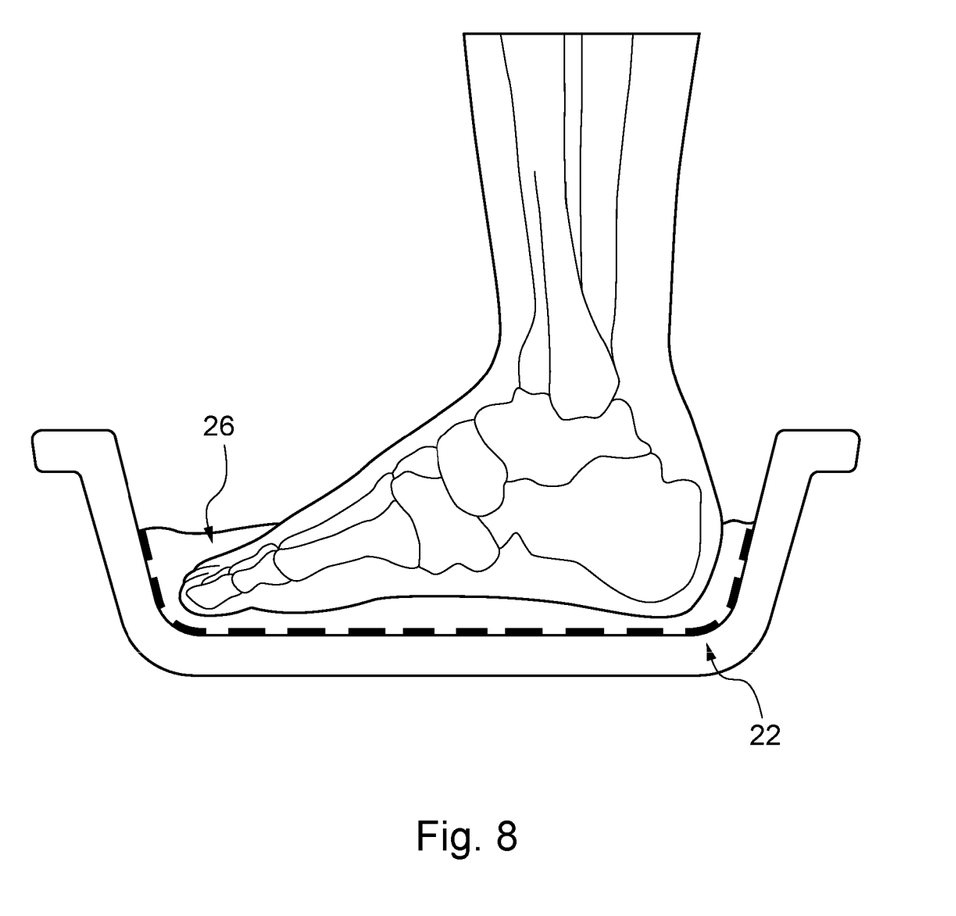
FIG. 8 (not forming part of the present invention) is a schematic cross-sectional view of an alternative application of the general concept of the present invention.

Finally, FIG. 8 shows an alternative application of the concept described above, but which does not form part of the present invention. Here, instead of a dental tray, a larger basin-like receptacle is provided to accommodate a foot. Ultrasound imaging elements 22 are provided over an inner surface of the base and side walls of the receptacle. The receptacle is provided with a gel-filled sac which fills approximately 50% of its internal volume. The principle of operation is similar to that of the dental tray 10 of the present invention insofar as both the surface topography and substructure of the foot can be virtually imaged. Compression of the soft tissue of the foot can also be simulated such that bespoke shoe insoles can be manufactured to provide optimal support and comfort for the wearer.

The invention claimed is:

1. A dental tray assembly for intraoral imaging of an edentulous dental arch and/or palate; the dental tray assembly comprising:
   (i) a base surface for facing, in use, a dental arch within an oral cavity;
   (ii) an opposing external surface;

(iii) an anterior wall connected to said base surface and extending arcuately on either side of a central axis coinciding, in use, with a labial frenulum, wherein the base surface and the anterior wall together define a concave trough for at least partially surrounding, in use, a dental arch within an oral cavity;

(iv) a posterior edge connecting opposing sides of the anterior wall and extending, in use, substantially perpendicular to the central axis; and (v) a gel-filled sac is removably placed within the arcuate trough to provide a deformable interface between the dental tray and a patient's edentulous arches and/or palate:

wherein a spaced-apart array of ultrasound imaging emitters is attached to the dental tray within the trough for emitting and receiving ultrasound signals, the received ultrasound signals being representative of a surface topography and/or sub-surface structures of an edentulous dental arch and/or palate to be imaged.

2. A dental tray assembly according to claim 1, wherein the array of ultrasound imaging emitters is spaced apart across an entirety of the base surface and/or the anterior wall.

3. A dental tray assembly according to claim 1, in which the gel is a water-based gel.

4. A dental tray assembly according to claim 1, in which the gel within the gel-filled sac is a heat-sensitive settable gel for forming an impression of anatomical surface features of the oral cavity including one or more of the group comprising the palate, ridges and sulci.

5. A dental tray assembly according to claim 1, in which the gel-filled sac is formed from a synthetic latex material.

6. A dental tray assembly according to claim 1, in which the gel-filled sac is dimensioned such that it fills the arcuate trough and extends above a height of the anterior wall.

7. A dental tray assembly according to claim 1, in which the gel-filled sac comprises an attached sheath adapted to envelop the dental tray.

8. A dental tray assembly according to claim 1, in which the ultrasound imaging emitters are non-piezoelectric.

9. A dental tray assembly according to claim 8, in which the ultrasound imaging emitters are printed on a flexible foil which is conformable to a concave internal surface of the dental tray.

10. A dental tray assembly according to claim 1, in which a handle portion projects away from the anterior wall and, in use, extends out of the oral cavity.

11. A dental tray assembly according to claim 10, in which a camera is located on the handle for detecting, in use, position of reference points on a patient's face relative to a patient's mouth.

12. A dental tray assembly according to claim 11, in which the camera is connectable to an external processing device.

13. A dental tray assembly according to claim 10, in which the ultrasound imaging emitters are connected to a power source located in the handle portion.

14. A dental tray assembly according to claim 13, in which an aperture is formed in the anterior wall to facilitate a physical connection between the power source and the ultrasound imaging emitters.

15. A dental tray assembly according to claim 13, in which the external processing device is a mobile or tablet device.

16. A dental tray assembly according to claim 1, in which the ultrasound imaging emitters are connectable to an external processing device.

17. A method of imaging edentulous arches and/or palate comprising the steps of:

(i) providing a dental tray in accordance with claim 1;

(ii) locating a gel-filled sac within the arcuate trough of the dental tray to provide a deformable interface between it and a dental arch and/or palate to be imaged;

(iii) applying a layer of gel to the exposed surface of the gel-filled sac;

(iv) introducing the dental tray into the oral cavity and moving it towards the dental arch and/or palate to be imaged such that the gel-filled sac is gently urged against and conforms to the shape of said dental arch and/or palate;

(v) activating the spaced-apart array of ultrasound imaging elements within the trough of the dental tray; and (vi) receiving a primary data set from the ultrasound imaging elements representative of the surface topography and/or sub-surface structures of the dental arch and/or palate to be imaged.

18. A method of imaging the edentulous arches and/or palate according to claim 17, in which the step of receiving a primary data set from the ultrasound imaging elements includes processing said data; or in which the step of processing the primary data set includes storing the processed data set in a memory for future use; or in which the step of processing the primary data set includes providing a display for displaying a synchronous rendered image of a patient's edentulous arches; or in which the step of locating a gel-filled sac within the arcuate trough of the dental tray is preceded by a step of enveloping the dental tray in a protective sheath; or the step of locating a gel-filled sac within the arcuate trough of the dental tray includes enveloping the dental tray in a protective sheath which is formed integrally with the gel-filled sac.

* * * * *